United States Patent [19]

Meilland et al.

[11] Plant 4,013

[45] Feb. 1, 1977

[54] ROSE PLANT—MEILIMONA VARIETY

[75] Inventors: Marie-Louise Meilland; Alain A. Meilland, both of Antibes; Michele Meilland Richardier, Tassin-la-Demi-Lune, all of France

[73] Assignee: The Conard-Pyle Company, West Grove, Pa.

[21] Appl. No.: 622,509

[22] Filed: Oct. 14, 1975

[30] Foreign Application Priority Data

Oct. 23, 1974 Morocco ..... 16931

[51] Int. Cl.[2] ..... A01H 5/00

[52] U.S. Cl. ..... Plt./15

[58] Field of Search ..... Plt./15

*Primary Examiner*—Robert E. Bagwill
*Attorney, Agent, or Firm*—Burns, Doane, Swecker & Mathis

[57] ABSTRACT

A rose plant of the Hybrid Tea Class, with yellow double flowers obtained by crossing the variety COED (seed parent) with an unnamed variety (pollen parent), which was obtained by pollination of the variety MEJENOR 552 by the variety MESHA 566, the result of which was fecundated by the variety VERLA.

14 Drawing Figures

SUMMARY OF THE INVENTION

The object of the present invention is a variety of rose-plant of the Hybrid Tea Class, with yellow double flowers, which is distinguishable from varieties already known in that Class and this kind of color, because of the following characteristics:

great originality of the Canary yellow coloring of its blooms;

specially elegant form of these blooms; and special aptitude of the plant to forcing.

In view of the characteristics mentioned above, the present invention answers the needs of the horticultural industry, for all uses, more especially for the production of cut flowers under glass.

The variety—object of the present invention—owes its origin to an operation of artificial pollination where two genitors were brought in, whose previous and respective study had allowed the anticipation, in their common descent, of the appearance of the characters sought.

The rose-plant chosen as female genitor (seed parent) was the variety COED, that chosen as male genitor (pollen) was the product of the pollination of the variety MEJENOR 552 by the variety MESHA 566, the result of which was fecundated by the variety VERLA.

The operation of artificial pollination thus performed can therefore be expressed by the following schematic formula:

COED × [(MEJENOR 552 × MESHA 566) × VERLA]

The technical tests (grafting inside or outside, with started eye-buds, dormant eye-buds, in heated greenhouses, in cold greenhouses . . . ) which were made to check the behavior and the yield-capacity of the variety just obtained, were conclusive and underlined the importance of creating this variety with a view to its industrial exploitation by the nurserymen, and especially by the producers of cut flowers under glass.

The characters and properties of this new variety, obtained as indicated above, are strictly transmissible by agamic means, also called asexual, i.e., by any means of vegetative propagation, and in particular by grafting an "eye" which will be called in the trade by the name of MEILIMONA 0880 F, and which will be found on industrial plants as well as on cut stems delivered subsequently in the trade. Thus will be obtained once again the variety of rose-plant—object of the patent—whose botanical and descriptive characteristics, observed on plants grown under glass, at Cap d'Antibes, Alpes-Maritimes, France, are listed below:

BRIEF DESCRIPTION OF DRAWINGS

The accompanying drawings show as nearly true as it is reasonably possible to make the same in a color illustration of this character, typical specimens of the flowers and foliage, illustrated in.

DETAILED DESCRIPTION OF DISCLOSURE

Figures 1, 2, 3, 4, 5, 6, 7, 8, 9, 10, 11, 12, 13, 14:
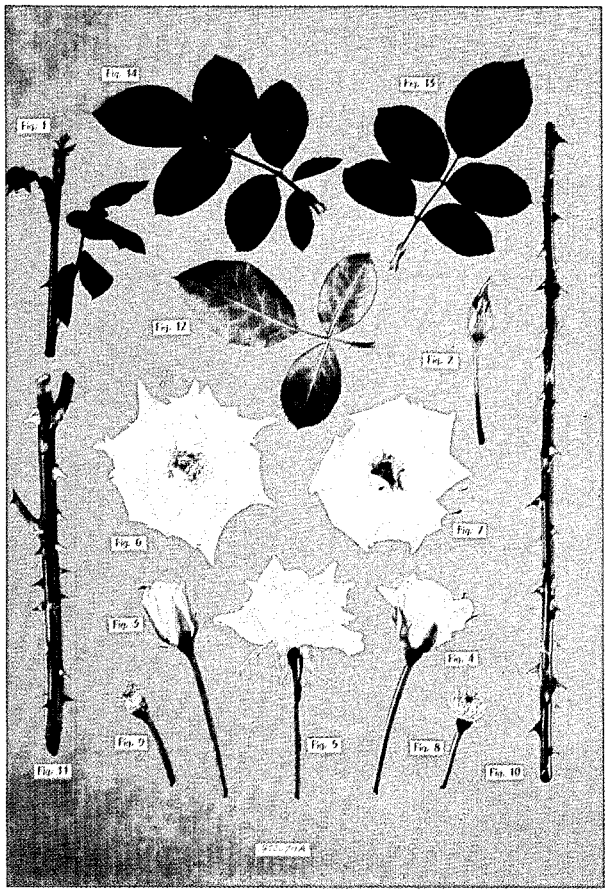
FIG. 1 — a specimen of a young shoot.
FIG. 2 — a specimen of a bud before the sepals open.
FIG. 3 — a specimen of a bud when the sepals open.
FIG. 4 — a specimen of a bud when the petals open.
FIG. 5 — a specimen of a flower in the course of opening.
FIG. 6 — a specimen of a fully open flower, flat view, inside.
FIG. 7 — a specimen of a fully open flower, flat view, outside.
FIG. 8 — a specimen of a receptacle showing the disposition of the stamens when the anthers burst open.
FIG. 9 — a specimen of a receptacle showing the disposition of the pistils (stamens removed) when the anthers open.
FIG. 10 — a portion of a flower-bearing stem.
FIG. 11 — a portion of a main stem.
FIG. 12 — a specimen of a leaf with 3 folioles, under surface.
FIG. 13 — a specimen of a leaf with 5 folioles, upper surface.
FIG. 14 — a specimen of a leaf with 7 folioles, upper surface.

The Chart used for the identification of the colors is that of the Royal Horticultural Society (R.H.S. Color Chart). The terminology preceding the numbered references, proper to this Chart, has been added to designate, in common terms, the corresponding colors.

Class: Hybrid Tea.

Plant:

*Height.*—On greenhouse plants cut down to about Om 85, the the length of the floral stems to be cut is between 60 and 80 cms.

*Habit.*—erect.

Branches:

*Color.*—Young stems: when the buds are forming, they are reddish on the side in the sun, and very light green on the shaded side. Then, they become uniformly light green. Mature wood: medium green 147/B (yellow green group).

*Prickels.*—Shape: upper edge — straight; lower edge — concave; base — obovate, narrow. Size: medium. Quantity: average. Color: on young stems — very light green, slightly pinkish at base, and yellow at the tip; on mature wood — havana brown, tip a little darker.

Leaves:

*Stipules.*—adnate, pectinate, fairly wide and linear.

*Petiole.*—inside: the bottom part is light green and the edges reddish brown, in the young foliage; the edges become medium green in the adult foliage and are glandular. Outside: light green with small hooked prickles, greenish yellow (young foliage) then very light straw (adult foliage). It forms, with the stem, an angle between 45° and 90°.

*Leaflets.*—Number: 3–5–7. Shape: on a standard-model leaf, situated at about ⅓ of a flower-bearing branch (first pair starting from the top). Top: more or less wide — symmetrical. Base: rounded — symmetrical. Shape as a whole: rounded oval, sometimes a little spear-shaped. Teeth: single — coarse. Texture: average to leathery. General effect: moderately ample and dense foliage, shiny for the young stems, dull for the adult foliage. Color: Young foliage; upper surface — dark green 137/A (green group); under surface — greyish green 191/B (greyed green group). Adult foliage; upper surface — dark green 147/A (yellow green group); under surface — greyish green 191/A (greyed green group).

It is to be noted that when growth starts, as also during the course of vegetation, the foliage of the young shoots is reddish purple, slightly mixed with very light green on the upper surface, and reddish purple on the under surface.

Inflorescence:

*Number of flowers.*—One flower per stem.

*Peduncle.*—Straight—moderately glandular yellow green, very light. Length: 7 to 8 cms.

*Sepals.*—Hairy, greenish inside; light green and smooth outside. The glandular edges are sometimes provided with a few appendages. They are fairly wide and tapered at the extreme point.

*Bud.*—Shape: oval. Length: 30 mm. on an average — outside the calyx when the first petal opens. Size: medium. Color: when opening — inside: Aureolin yellow 12/B (yellow group) on the edge, and 12/A (yellow group) at center; outside: light yellow 11/A (yellow group).

*Flower.*—Form — When the first outer petals open, their tips are pointed and their lateral edges are reflexed; the center ones remain high. Open, the flower looks like a hollow bowl, and stamens are visible. Double flower — diameter: 10/11 cms. on an average; color: when opening; inside: Aureolin yellow 12/B (yellow group) in the upper part and lateral edges; 12/A (yellow group) towards the center and the base; outside: light yellow 11/A (yellow group) slightly touched up with 12/B. In the course of opening — inside: canary yellow 9/B (yellow group) at center and base, 9/C towards the top; outside: canary yellow 9/C more or less touched up with 9/B going towards the base. When fully open — inside: light sulphur yellow 6/C (yellow group) towards the base and the center and 6/D towards the top and the lateral edges; outside: pale yellow 5/D (yellow group).

*Fragrance.*—Light, sugary. Long lasting quality of the flowers when cut.

*Corolla.*—Petals — Texture: firm. Shape: those of the exterior periphery are broadly rounded at the top; the base is narrow. The center petals are rounded at the top and wedge-shaped at the base; lateral edges reflexed. Number: 35 on an average. The petals drop off cleanly. Stamens: number — 140 on an average; anthers — normal, yellow; filaments — yellow. Pistils: number — 100 on an average. Stigmas: yellowish over the orifice of the receptacle, but under the level of the anthers. Styles: fairly short, free, slightly twisted, whitish at base and fuchsia at top. Receptacle: light green, it is narrow and in the shape of a pitcher when cut longitudinally.

Development:

*Vegetation.*—Vigorous

*Blooming.*—Continuous underglass.

We claim:

1. A new and distinct variety of Hybrid Tea rose-plant of vegetative reproduction, characterized by the fact that, from the physical point of view, the plant, with medium green adult wood, is erect, the flower is double, canary yellow; the petals are firm;

from the biological point of view, this rose-plant is of vigorous vegetation, blooms continuously, is very good for forcing; good resistance to diseases, its flowers last a long time, either when cut, or on the plant, and its petals drop off cleanly;

substantially as shown and described.

* * * * *